United States Patent [19]

Signorini

[11] Patent Number: 5,020,679
[45] Date of Patent: Jun. 4, 1991

[54] NURSING APPARATUS

[76] Inventor: Alberto Signorini, Rua Engenheiro Alvaro Niemeyer, 113, Sao Conrado, 22600 Rio de Janeiro, RJ, Brazil

[21] Appl. No.: 582,132

[22] Filed: Sep. 12, 1990

Related U.S. Application Data

[63] Continuation of Ser. No. 345,723, Jun. 2, 1989, abandoned.

[30] Foreign Application Priority Data

Jun. 8, 1988 [BR] Brazil .................................. 8802780

[51] Int. Cl.⁵ .......................... A61J 9/00; A61J 11/04
[52] U.S. Cl. ..................................... 215/11.1; 215/335
[58] Field of Search .............................. 215/11.1–11.6, 215/335; 604/73–75

[56] References Cited

U.S. PATENT DOCUMENTS

| | | | |
|---|---|---|---|
| 1,069,153 | 8/1913 | Lovell | 215/335 |
| 1,613,826 | 1/1927 | Hind | 215/335 X |
| 2,448,569 | 9/1948 | Allen | 215/11.1 |
| 2,822,102 | 2/1958 | Holland | 215/11.1 |
| 3,076,574 | 2/1963 | Woodbury, Jr. | 215/11.1 |
| 3,434,615 | 3/1969 | Barletta | 215/335 X |
| 3,899,096 | 8/1975 | Marco | 215/335 X |
| 3,977,405 | 8/1976 | Yanase | 604/74 |
| 4,573,969 | 3/1986 | Schlensog et al. | 604/74 |

FOREIGN PATENT DOCUMENTS

| | | | |
|---|---|---|---|
| 492173 | 4/1953 | Canada | 215/11.1 |
| 515466 | 8/1955 | Canada | 215/11.1 |
| 746707 | 11/1966 | Canada | 215/11.1 |

*Primary Examiner*—Sue A. Weaver
*Attorney, Agent, or Firm*—Pettis & McDonald

[57] ABSTRACT

A nursing bottle having an unthreaded neck portion to which an anatomically designed nipple is fixed by means of cap and a counter-cap. An accessory is provided to permit the nursing bottle to be used as a component of a practical and efficient breast pump. The body of the bottle can be utilized as a glass to teach the child to drink in an adult way.

4 Claims, 2 Drawing Sheets

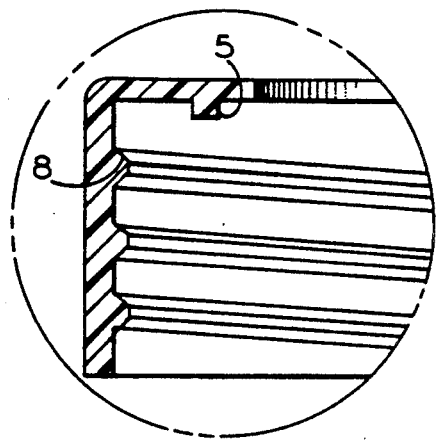
FIGURE 2
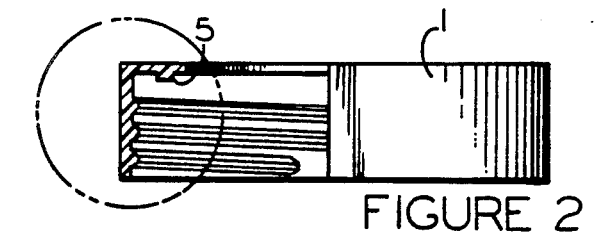
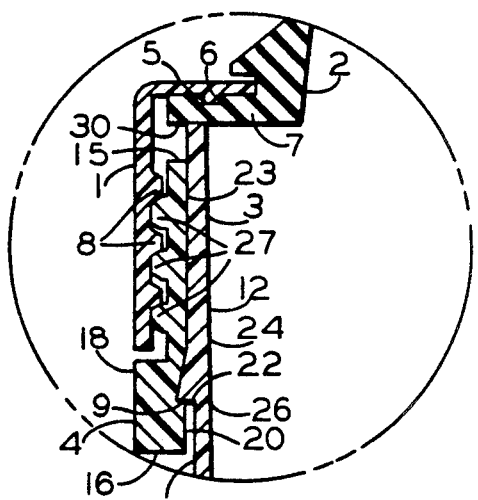
FIGURE 2A
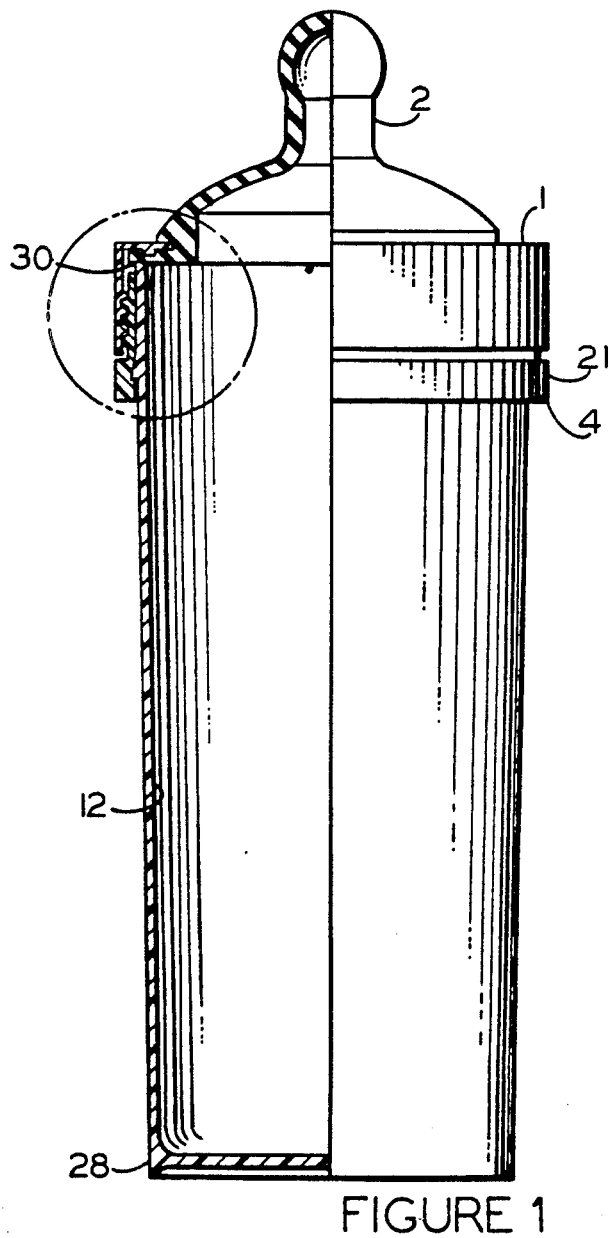
FIGURE 1A
FIGURE 1
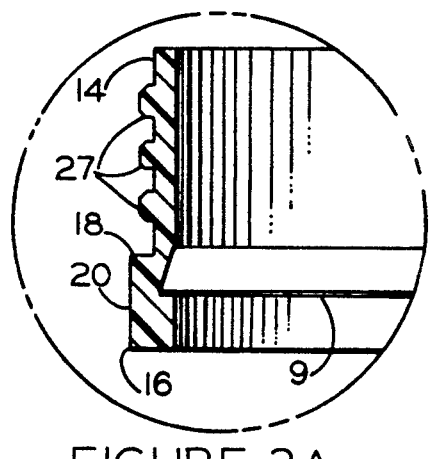
FIGURE 3A
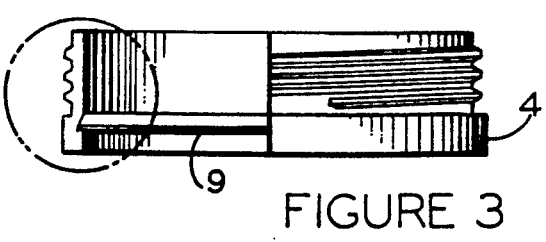
FIGURE 3

NURSING APPARATUS

This is a continuation of application Ser. No. 07/345,723, filed Jun. 2, 1989, now abandoned.

BACKGROUND OF THE INVENTION

Nursing bottles intended for feeding newborns are well known. Basically, such "baby bottles" are formed of a body or flask of diverse forms with a threaded neck to which a cap is screwed, thereby fixing the nipple to the neck opening. An overcap or hood is provided to protect the nipple from outside agents. In general, nursing bottles have not had any major developments in their basic form for many years. The traditional bottle shape has been preserved.

The necks of prior art bottles are generally of standard diameters. The neck is formed by narrowing the body in the upper portion so as to form the characteristic shape of a baby bottle. These bottles have a thread on their neck portion and, immediately under the same, an expansion to form the body of the flask. This arrangement can encourage the proliferation of germs and bacteria and makes the bottle difficult to clean. Specifically designed brushes are available for cleaning such bottles. Because of the narrowed neck, dishwashers fail to do a proper job.

The present invention provides a body which, contrary to the usual prior art design, does not have the shape of a bottle but of a glass or cup. The bottle body does not have internal or external threads. It is formed with smooth walls and without an abrupt increase in diameter. This assures a more hygienic container that requires no special system to clean. It may be washed with the same ease as a traditional glass. According to the invention, the nipple-holding cap is not screwed directly on a body or neck thread. Securement is by a separate counter-cap which is slid upward onto the body, from the second end of the bottle body until the counter-cap engages a stop means that prevents the counter-cap from moving any further upward. The stop means is so located that the counter-cap is maintained in a spaced apart relationship with the first end of the bottle body. By preventing the counter-cap from moving further toward the first end of the bottle body, it retains the counter-cap on the body and permits the cap-and-nipple set to be screwed on tightly. The design of the tooth assures no slippage as the cap is screwed into place, but permits removal of the counter-cap with a slight, downward touch.

When the counter-cap is withdrawn, both cap and counter-cap can be easily washed and sterilized, also allowing the nursing bottle body to be transformed in a classic, smoothedged glass which the child may thereafter use to learn how to drink out of a normal drinking glass.

SUMMARY OF THE INVENTION

A principal objective of this invention is to create a new commercial product which constitutes a nursing bottle with a body, or flask, which is completely smooth, has a wide mouth and therefore has the inner portion which is easily accessible for cleaning. The body or flask of the present invention is wider than the traditional top of a baby bottle. It tapers slightly from the upper open end to the bottom end. In this respect, the body is an inverted hollow frustum.

The sealing of the nipple against the body is obtained through the pressure between the cap and the counter-cap, this latter being introduced from bottom to top, on the frustum body. The counter-cap comprises a sleeve having exterior and interior surfaces and a first section and a second section. As the counter-cap is slid upward on the bottle body, a stop means is engaged preventing the counter-cap from advancing further, causing the first end of the bottle body to be halted at a stop position, such that the first end of the counter-cap is proximal to and spaced apart from the open end of the bottle body. The stop means comprises a first engaging means formed on the exterior surface of the bottle body, and a second engaging means formed solely on the interior surface of the counter-cap. When the counter-cap is in the stop position, the first end of the counter-cap is spaced radially outwardly from the first engaging means. In the stop position the first end of the counter-cap is intermediate the first end of the bottle body and the first engaging means, and the first end of the counter-cap also extends upwardly beyond the first engaging means on the outer surface of the body. The stop means retains the counter-cap so as to support the action of screwing on the nipple-holding cap to assure a good seal.

It is another objective of the invention to provide an accessory that transforms the nursing bottle into a functional breast pump for a mother's bosom.

This invention consists of the use of the body of the nursing bottle as a cylinder inside of which runs a specially shaped piston. The piston is held against the mother's breast with a slight pressure to form a seal. When the bottle body is pulled away from the breast, a sufficient vacuum is obtained to extract milk from the breast.

After use of the accessory, the piston is removed from the set, the counter-cap is slid on the body, the nipple-holding cap is screwed into place and the baby may be given the mother's milk still warm and without hazard of contamination since the milk has not been transferred to another nursing bottle.

These and other objects of the invention will become more apparent to those skilled in the art by reference to the following detailed description when viewed in light of the accompanying drawings.

BRIEF DESCRIPTION OF THE DRAWINGS

FIG. 1 is a side elevation view partly in section;

FIG. 2 is an elevational view of a cap member partly in section;

Figure 4:
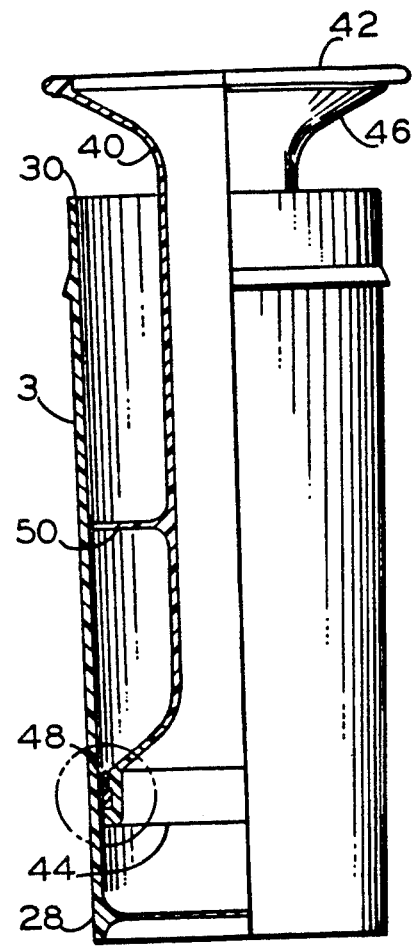
Figure 4A:
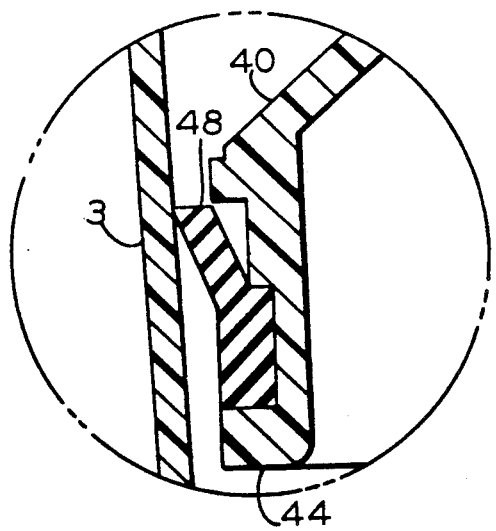

Detail A is an enlarged portion of FIG. 2;

Detail B is an enlarged portion of FIG. 1;

FIG. 3 is an elevational view of a counter-cap partly in section;

Detail C is an enlarged portion of FIG. 3;

FIG. 4 is an elevational view of a breast pump partly in section; and

Detail D is an enlarged detail of a portion of FIG. 4.

DESCRIPTION OF THE PREFERRED EMBODIMENT

In the following description, like numerals indicate like parts in all of the figures. FIG. 1 is a partial section of the nursing bottle and shows the components assembled. FIG. 2 and Detail A show a nipple-holding cap 1 having screw threads 8, and further show the annular tooth 5 of the nipple holding cap 1 which enters or embeds into a circular reception groove 6 formed in correspondence on the upper surface of the flange 7 of nipple 2. FIG. 3 and its respective Detail C show a counter-cap 4 with a tooth 9 formed solely on the interior surface of the counter-cap 4 The Detail B is an enlarged view of the sealing set and includes cap 1, nipple 2, body 3, and the counter-cap 4.

FIG. 1 illustrates the bottle body 3 that comprises a hollow frustum having an exterior surface 11 and an interior surface 12, a first end 30 that is open and a second end 28 that is closed, and a first portion 24 and a second portion 26. The first end 30 has a larger circumference than the second end 28 creating the taper of an inverted frustum.

Details B and C illustrate the counter-cap 4, which comprises a sleeve that is a hollow frustum having a taper similar to that of the bottle body 3. The counter-cap 4 further comprises an exterior surface 21, an interior surface 23, a first end 14, a second end 16, a first section 18, and a second section 20. The exterior surface 21, of the first section 18 of the counter-cap 4 has threads 27 formed thereon.

When the counter-cap 4 is mounted on the second end 28 of the bottle body 3 and slid upward, a stop means is engaged preventing the counter-cap from advancing further. When the first end 14 of the counter-cap 4 cannot be advanced any further, the position of the counter-cap 4 on the bottle body 3 defines a stop position. When the counter-cap 4 is in the stop position, the first end 14 of the counter-cap 4 is proximal to and spaced apart from the first end 30 of the bottle body 3. The stop means comprises a first engaging means formed on the exterior surface 11 of the bottle body 3, and a second engaging means formed solely on the interior surface 23 of the counter-cap 4.

In the preferred embodiment, the first engaging means comprises an annular tooth 22 on the exterior surface 11 of the bottle body 3. The tooth 22 is interposed between the first portion 24 and the second portion 26 of the bottle body 3. The tooth 22 is defined by the circumference of the exterior surface of the bottle body 3 being greater about the first portion 24 adjacent to the tooth 22 than around the second portion 26 adjacent the tooth 22. The second engaging means comprises an opposing annular tooth 9, formed solely on the interior surface 23 of the counter-cap 4. The tooth 9 is interposed between the first section 18 and the second section 20 of the counter-cap 4. The tooth 9 is defined by the first section 18 of the counter-cap 4 adjacent to the tooth 9 having an interior circumference greater than the interior circumference of the second section 20 of the counter-cap 4 adjacent to the tooth 9. The stp means therefore comprises the engagement of tooth 9 with tooth 22.

When the counter-cap 4 is in the stop position, the first end 14 of the counter-cap 4 is located radially outwardly from the tooth 22. In addition, when the counter-cap 4 is in the stop position, the first end 14 of the counter-cap 4 is intermediate the first end 30 of the bottle body 3 and the tooth 22, 22, and also the first end 14 of the counter-cap 4 extends upwardly beyond the tooth 22 which results in the top surface 15 of the counter-cap 4 being spaced apart from the tooth 22.

Detail B demonstrates the coupling between cap 1 and nipple 2 This coupling, or embedding, assures that nipple 2 is fixed on the cap 1 so that the nipple 2 can be manipulated or screwed on the nursing bottle body without manual contact, thus assuring sterility. The sealing of the nipple 2 against the body 3 is accomplished by first placing the nipple holding cap 1 over the nipple 2 so that the tooth 5 of the nipple holding cap 2 is embedded in the groove 6 of the flange 7 of the nipple 2. This will assure that the nipple 2 remains in position. When the counter-cap 4 has been mounted on the bottle body 3 so that the stop means is engaged and the counter-cap 4 is placed in the stop position, the first end 14 of the counter-cap 4 remains in spaced apart relationship from the first end 30 of the bottle body 3 and thus is also in spaced apart relationship with the flange 7 of nipple 2. The nipple holding cap 1 with nipple 2 mounted therein is placed on the first end 30 of the bottle body 3. The screw threads 8 of the nipple holding cap 1 are threadably engaged with the screw threads 27 of the counter-cap 4 to define an attaching means. By holding the counter-cap 4 to prevent it from twisting, the nipple holding cap 1 may be screwed tightly to the counter-cap 4 causing the flange 7 of the nipple 2 to come into sealing contact with the first end 30 of the bottle body 3.

FIG. 4 is a partial section of the nursing bottle transformed into a breast pump, showing the accessory and a sealing system. Using the body 3 of the nursing bottle as a cylinder, with the piston 40 and its respective sealing ring 48 inside of body 3, the breast pump of FIG. 4 and Detail D is obtained.

The piston 40 is a hollow cylinder that has a first open end 42 and a second open end 44, which is sized to be slidably inserted within the bottle body 3 with the first end 42 projecting outwardly from the open end 30 of the bottle body 3 when the second end 44 is adjacent to the second end 28 of the bottle body 3. The first end 42 of the piston 40 is formed outwardly in a generally cupped shaped configuration 46 and is in fluid flow communication with the second end 44 of the piston 40 and, therefore, also with the interior of the second end 28 of the bottle body 3. The second end 44 of the piston 40 has a sealing means 48 between the piston 40 and the bottle body 3, such that when the first end 42 of the piston 40 is sealed by placement on the breast, movement of the second end 44 of the piston 40 away from the second end 28 of the bottle body 3 and within the hollow piston 40. An annular stabilizing strut 50 extends radially from the piston to a point proximal to the interior surface of the bottle body 3. This stabilizer helps the piston retain its proper alignment while being moved within the bottle body 3.

Placing the first end 42 of the piston 40 of the breast pump as seen in FIG. 4 on the mother's bosom so as to cover the mammilla, milk can be extracted from the bosom by holding the piston edge 4 with the thumb and the forefinger of one hand and pulling the bottle body outward with the other hand.

In a general manner, while a preferred embodiment of the invention has been disclosed, it should be understood that the invention is not limited to such an embodiment as there may be changes made in the arrangement, disposition and location of the parts without departing from the principle of the present invention as comprehended within the scope of the accompanying claims.

I claim:
1. A nursing device comprising:
a bottle body comprising a hollow frustum having an exterior and an interior surface and having first and second ends, said first end being open and said second end being closed, said second end of said bottle body having a smaller circumference than said first end of said bottle body, and said bottle body having a first portion and a second portion;

a counter-cap comprising a sleeve having exterior and interior surfaces, having a first end and a second end, and having a first section and a second section, said counter-cap so sized and configured that said first end of said counter-cap may be slidably mounted over said second end of said bottle body such that said counter-cap may be slid toward said first end of said bottle body to a stop position, such that said first end of said counter-cap is proximal to and spaced apart from said first end of said bottle body;

a stop means comprising a first engaging means and a second engaging means, said first engaging means located on said exterior surface of said bottle body intermediate said first end and said second end of said bottle body, and said second engaging means formed solely on said interior surface of said counter-cap intermediate said first end and said second end of said counter-cap, such that when said counter-cap is mounted on said bottle body, said first end of said counter-cap is held in spaced apart relation from said first end of said bottle body, said first end of said counter-cap is intermediate said first end of said bottle body and said first engaging means, said first end of said counter-cap being located radially outwardly from said first engaging means on said bottle body, and said first end of said counter-cap extending upwardly beyond said first engaging means;

a nipple removably sealed to said first end of said bottle body;

a nipple holding cap to which said nipple may be removably mounted, said cap having an interior surface; and an attaching means wherein said nipple holding cap may be removably attached to said counter-cap, such that said nipple is removably sealed in liquid flow relationship to said first end of said bottle body.

2. A nursing device as in claim 1 wherein said first engaging means comprises an annular tooth located on said exterior surface of said bottle body, wherein said first portion of said bottle body adjacent said tooth has an exterior circumference greater than the exterior circumference of said second portion of said bottle body adjacent said annular tooth, thus defining said annular tooth interposed therebetween; and said second engaging means comprises an opposing annular tooth on said interior surface of said counter-cap, wherein said first section of said counter-cap has an interior circumference adjacent said tooth greater than the interior circumference of said second section of said counter-cap adjacent said tooth, thus, defining said annular tooth interposed therebetween, said bottle body and said counter-cap so dimensioned that when said first end of said counter-cap is slidably mounted over said second end of said bottle body, said tooth of said bottle body engages said opposing tooth of said, counter-cap such that said counter-cap cannot be advanced further.

3. A nursing device as in claim 1 wherein said attaching means for said nipple holding cap further comprises screw threads formed about said exterior surface of said counter cap sleeve proximal to said first end of said sleeve, and screw threads formed on said interior surface of said nipple holding cap such that said screw threads of said nipple holding cap may be removably engaged with said screw threads of said counter cap, whereby said nipple when mounted in said nipple holding cap is sealingly connected to said first end of said bottle body.

4. A nursing device as in claim 1 wherein said nipple holding cap further comprises a top portion having an interior surface and a nipple receiving hole therethrough and a depending annular skirt portion having interior threads thereon, and an annular tooth extending downward from said interior surface of said top portion intermediate said nipple receiving hole and said annular skirt portion, and said nipple further comprises an annular flange having a lower surface sized and configured such that said lower surface of aid flange engages said first end of said bottle body, said flange having an upper surface in which is formed an annular groove sized and configured such that said tooth of said nipple holding cap engages said annular groove of said nipple when said nipple is inserted within said nipple holding cap.

* * * * *

UNITED STATES PATENT AND TRADEMARK OFFICE
CERTIFICATE OF CORRECTION

PATENT NO. : 5,020,679
DATED : June 4, 1991
INVENTOR(S) : Alberto Signorini

It is certified that error appears in the above-identified patent and that said Letters Patent is hereby corrected as shown below:

Claim 4, column 6, line 38, "aid" should be "said".

Signed and Sealed this

Sixth Day of October, 1992

Attest:

DOUGLAS B. COMER

*Attesting Officer*  *Acting Commissioner of Patents and Trademarks*